(12) United States Patent
Heipp et al.

(10) Patent No.: US 9,134,219 B2
(45) Date of Patent: Sep. 15, 2015

(54) PERMEABILITY FLOW CELL AND HYDRAULIC CONDUCTANCE SYSTEM

(75) Inventors: Paul S. Heipp, Blackwood, NJ (US); Deepak Sharma, Flemington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 362 days.

(21) Appl. No.: 13/600,451

(22) Filed: Aug. 31, 2012

(65) Prior Publication Data

US 2014/0060156 A1 Mar. 6, 2014

(51) Int. Cl.
*G01N 15/08* (2006.01)
(52) U.S. Cl.
CPC ............ *G01N 15/0826* (2013.01); *G01N 15/08* (2013.01); *G01N 15/082* (2013.01); *G01N 15/0806* (2013.01)

(58) Field of Classification Search
CPC .............. G01N 15/08; G01N 15/0806; G01N 15/0826; G01N 15/082; G01N 15/088; G01N 2015/086; G01F 1/36
USPC ................................ 73/38, 864.91, 865.6, 37
See application file for complete search history.

(56) References Cited

U.S. PATENT DOCUMENTS

| | | | |
|---|---|---|---|
| 2004/0189988 A1* | 9/2004 | Scaduto | 356/244 |
| 2007/0098652 A1* | 5/2007 | Chow et al. | 424/52 |
| 2008/0275653 A1 | 11/2008 | Cypes et al. | |
| 2009/0186090 A1* | 7/2009 | Zaidel et al. | 424/489 |

OTHER PUBLICATIONS

Ozok, A.R. et al., "Comparison of the in vitro permeability of human dentine according to the dentinal region and the composition of the simulated dentinal fluid"; Journal of Dentistry 30; 2002; pp. 107-111.*
Niaxy M. A. et al., "The role of Adhesive systems and dentin desensitizers in altering the permeability of human dentin"; Cairo Dental Journal (25) No. (3); Sep. 2009; pp. 433-442.*
Cherng, Aishuan Maria, et al.; Reduction in Dentin Permeability Using a Slurry Containing Dicalcium Phosphate and Calcium Hydroxide; Wiley InterScience; Published Feb. 7, 2006; pp. 291-295. (www. Interscience.wiley.com).
Ishihata, Hiroshi; et al.; Effect of desensitizing agents on dentin permeability; American Journal of Dentistry, vol. 22, No. 3, Jun. 2009; pp. 143-146.
Gregoire, Genevieve, et al.; Effect of self-etching adhesives on dentin permeability in a fluid flow model; The Journal of Prosthetic Dentistry, vol. 93, No. 1; Jan. 2005; pp. 56-63.
Ozok, A.R., et al.; Effect of Dentinal Fluid Composition on Dentin Demineralization in vitro; J. Dent. Res 83(11); 2004, pp. 849-853.
Cherng, A.M., et al.; Reduction in dentin permeability using mildly supersaturated calcium phosphate solutions; Archives of Oral Biology vol. 49; 2004; pp. 91-98.
Ishihata, Hiroshi; et al.; Effects of Glutaraldehyde, HEMA and Gluma Desensitizer on in vitro dentin permeability; Int'l. Journal of Contemporary Dentistry; 2(1); 2011; pp. 3-8.

(Continued)

*Primary Examiner* — Hezron E Williams
*Assistant Examiner* — Marrit Eyassu

(57) ABSTRACT

The present invention relates to devices and methods for measuring the permeability of dentin. More particularly, the invention relates to devices and methods of quickly and accurately measuring the permeability of dentin using a flow cell.

11 Claims, 7 Drawing Sheets

(56) References Cited

OTHER PUBLICATIONS

Sauro, Salvatore, et al.; Ultramorphology and dentine permeability changes induced by prophylactic procedures on exposed dentinal tubules in middle dentine; Med. Oral Patol Oral Cir. Bucal; 16(7); Nov. 1, 2011; pp. 1022-1130.

Komabayashi, Takashi, et al.; Dentin Permeability Reduction by a Sequential Application of Calcium and Fluoride-Phosphate Solutions; J. Dent. 38(9); Sep. 2010; pp. 736-741.

Bouillaguet, Serge, et al.; Effects of Nd:YAG (1.06 μm) and CTH:YAG (2.1 μm) laser irradiations on dentin permeability in vitro; Acta. Med Dent. Helv. 4; 1999; pp. 135-140.

Chiang, Y.C., et al.; A Novel Mesoporous Biomaterial for Treating Dentin Hypersensitivity; J. Dent. Res. 89(3); 2010; pp. 236-240.

Santiago, Sergio Lima, et al.; Effect of Commercially Available and Experimental Potassium Oxalate-Based Dentin Desensitizing Agents in Dentin Permeability: Influence of Time and Filtration System; Braz. Dent. J. 17(4); 2006; pp. 300-305.

Ozok, A. R., et al.; Comparison of the in vitro permeability of human dentine according to the dentinal region and the composition of the simulated dentinal fluid; Journal of Dentistry 30; 2002; pp. 107-111.

Ling, A. L.; Fluid Flow Measurement Selection and Sizing (Engineering Design Guideline); KLM Technology Group Sdn. Bhd.; Mar. 2007; p. 1-17.

Wang, Zhejun, et al.; Effect of desensitising toothpastes on dentinal tubule occlusion: A dentine permeability measurement and SEM in vitro study; Journal of Dentistry 38; 2010; pp. 400-410.

Kim, Sun-Young, et al.; Real-time measurement of dentinal fluid flow during amalgam and composite restoration; Journal of Dentistry 38; 2010; pp. 343-351.

Bernard Ciucchi et al., "Dentinal Fluid Dynamics in Human Teeth, In Vivo", Journal of Endodontics, vol. 21, No. 4, Apr. 1995, pp. 191-194.

E.L. Pashley, et al., "Dentin Permeability: Sealing the Dentin in Crown Preparations", Operative Denstistry, 1992, 17, pp. 13-20.

Pashley, D.H., et al.; "Regional variability in the permeability of human dentine." Archives of oral biology 32.7 (1987): 519:523. p. 519, col. 2, paragraph 3; p. 520; figure 1; p. 521, figure 3.

Hanks, CT, et al. "Permeability of biological and synthetic molecules through dentine." Journal of oral rehabilitation 21.4 (1994): 475-487. pp. 476, 478.

Kolker, JL, et al.; "Effect of desensitizing agents on dentin permeability and dentin tubule occlusion." Journal of Adhesive Dentistry 4 (2002): 211-222. pp. 2-3.

Ghazali, FBC. "Permeability of dentine." The Malaysian journal of medical sciences; MJMS 10.1 (2003); 27. pp. 28-30.

Greenhill, JD, et al., "The effects of desensitizing agents on the hydraulic conductance of human dentin in vitro." Journal of Dental Research 60.3 (1981); 686-698.

\* cited by examiner

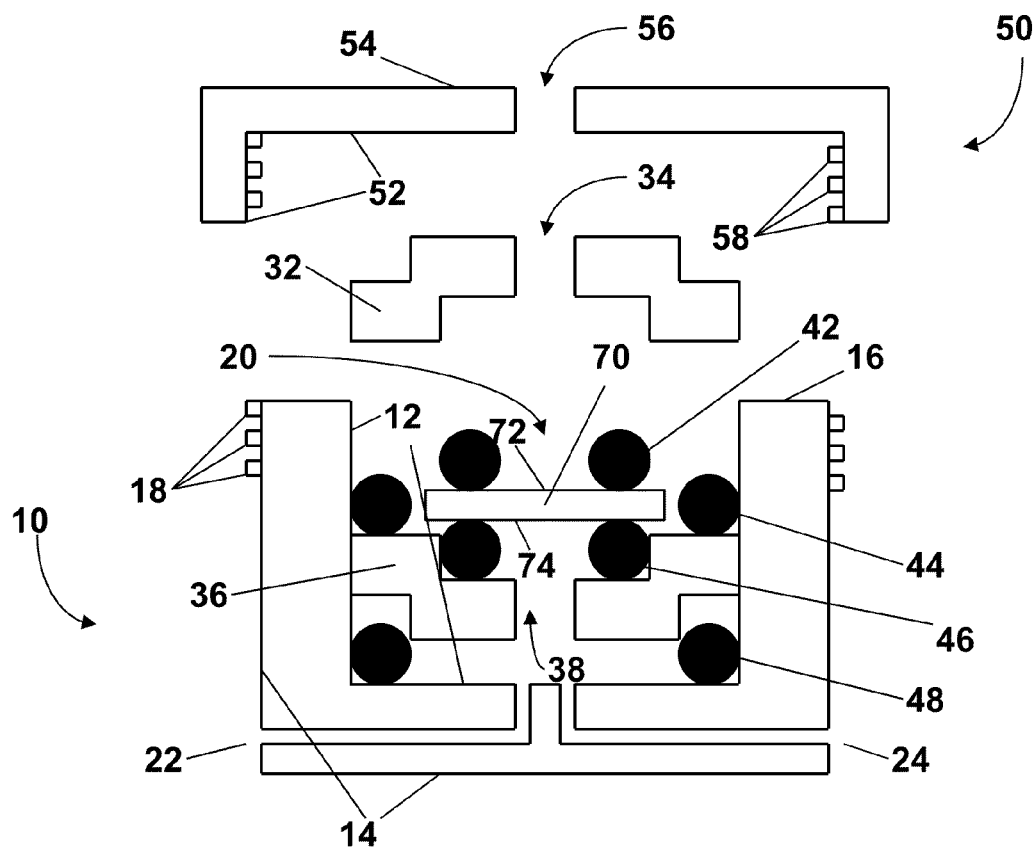
FIG. 1: Prior Art
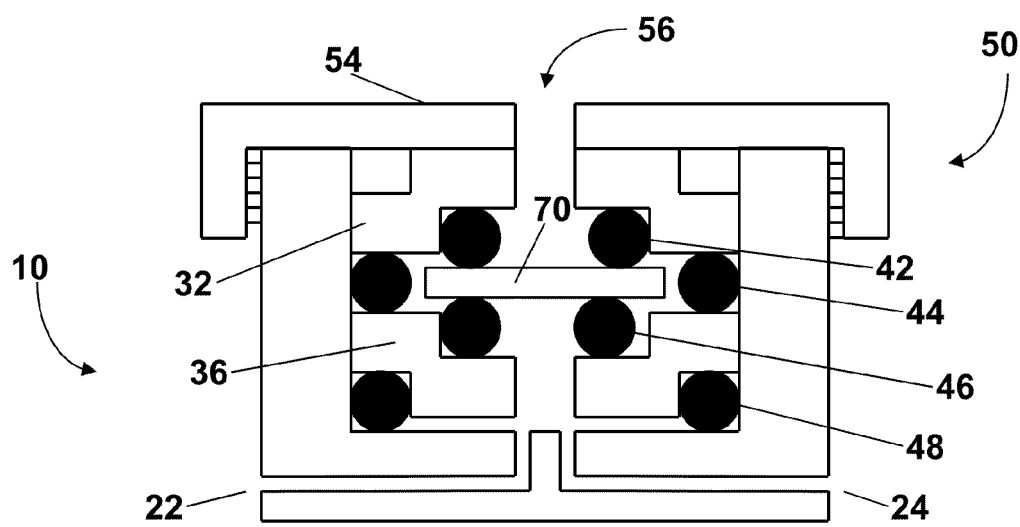
FIG. 2: Prior Art

Δh is measured from the fluid level of fluid 232 to top of dentin sample 190 in flow cell 100.

PERMEABILITY FLOW CELL AND HYDRAULIC CONDUCTANCE SYSTEM

FIELD OF THE INVENTION

The present invention relates to devices and methods for measuring the permeability of dentin. More particularly, the invention relates to devices and methods of quickly and accurately measuring the permeability of dentin using a flow cell.

BACKGROUND OF THE INVENTION

Tooth sensitivity affects numerous people. It is often caused by eating or drinking something hot, cold, sweet or acidic. Under normal conditions, the papal chamber, which houses the blood vessels and nerves, is surrounded by the dentin, which in turn is covered by the enamel in the tooth crown, and the gums that surround the tooth. Over time, the enamel covering can get thinner, thus providing less protection. The gums can also recede over time, exposing the underlying root surface dentin.

The dentin contains a large numbers of pores or tubule orifices that run from the outside of the tooth to the nerve at its center. When the dentin is exposed, these tubule orifices can be stimulated by temperature changes or certain foods. The hydrodynamic theory of dentin sensitivity states that stimuli applied to exposed dentin tubule orifices cause a movement of fluids in the tubules which, in turn, stimulates nerves in the pulp.

The well-know Pashley method for determining dentin permeability has been used as an in vitro model for screening agents which have been used to desensitize dentin. In this method, fluid is forced from an inlet across (or through) one side of a dentin disc sample to the other side and, then, its flow rate measured to determine the rate of fluid flow across the dentin sample. The prepared disc sample of dentin is secured in a split-chamber device, clamped between two paired "O" rings.

Certain limitations, however, exist regarding the Pashley method and generally relate to inherent inaccuracies affecting the overall accuracy of the method's permeability measurements. Moreover, the design of the flow cell used in the Pashley method does not allow for easy removal of the dentin sample during dentin permeability analysis to, for example perform further challenge to the dentin sample's surface and, then, return the dentin sample back to the flow cell for continued analysis.

Another limitation of the Pashley method relates to its inability to standardize the flow rates obtained across different dentin samples when permeability data for more than one dentin sample is necessary or desired.

As a result of these limitations, large sample sizes are required to achieve statistically significant dentin permeability readings.

The search for faster and more accurate methods of measuring the permeability of dentin using a modified flow cells and/or permeability measurement methods continues. Desired aspects for these methods include high accuracy and throughput (i.e., performing technology testing quickly and reliably producing sound data), data separation, error reduction, robustness, repeatability, and use with additional testing methods.

SUMMARY OF THE INVENTION

The present invention relates to devices, apparatus and methods for measuring the permeability of dentin.

In one embodiment, the present invention relates to a flow cell for measuring hydraulic conductance of dentin samples, comprising:
  a. a flow inlet channel;
  b. a flow outlet channel in flow communication with the flow inlet channel;
  c. at least one dentin sample securing mechanism positioned between the flow inlet channel and the flow outlet channel for securing a dentin sample; and
  d. at least one venting channel having an inner opening from which the venting channel extends outwardly from the flow cell, the venting channel positioned for receiving any air in the form of at least one air bubble that might accumulate under a dentin sample secured by the securing mechanism after introduction of a fluid into the flow cell through the flow inlet channel,
wherein the venting channel forms a positive angle $\theta$ relative to a bottom side of a horizontal cross-sectional plane through the bottom component, which horizontal cross-sectional plane intersects the inner opening of the venting channel such that the angle $\theta$ ranges from greater than about 0° to less than about 90°, the angle $\theta$ being measured counter clockwise from the bottom side of the horizontal cross-sectional plane and having its vertex at the point of intersection of the inner opening and the horizontal cross-sectional plane.

In another embodiment, the present invention relates to a flow cell for measuring hydraulic conductance of a dentin sample, comprising:
  A. a bottom component comprising:
     i. an inner chamber;
     ii. at least one flow inlet channel in flow communication with the inner chamber;
     iii. at least one flow outlet channel in flow communication with the flow inlet channel and the inner chamber;
     iv. at least one venting channel in flow communication with the inner chamber and having an inner opening where the venting channel joins with the inner chamber; and
     v. an opening at the top of the bottom component for accessing the inner chamber,
  B. a removable lid for covering the opening of the bottom component, the lid having a flow outlet channel positioned for receiving and permitting the outflow of fluid diffusing through (or across) the dentin sample from the flow inlet channel; and
  C. at least one washer adjacent to the lid and/or to the bottom component for securing the dentin sample within the flow cell,
wherein the venting channel forms a positive angle $\theta$ relative to a bottom side of a horizontal cross-sectional plane through the bottom component, which horizontal cross-sectional plane intersects the inner opening of the venting channel such that the angle $\theta$ ranges from greater than about 0° to less than about 90°, the angle $\theta$ being measured counter clockwise from the bottom side of the horizontal cross-sectional plane and having its vertex at the point of intersection of the inner opening and the horizontal cross-sectional plane.

In a further embodiment, the present invention relates to an apparatus for measuring hydraulic conductance of dentin samples, comprising;
  A. a flow cell comprising:
     a. a bottom component comprising:
        i. an inner chamber;
        ii. at least one flow inlet channel in flow communication with the inner chamber;
        iii. at least one venting channel in flow communication with the inner chamber and having an inner opening where the venting channel joins with the inner chamber wherein the venting channel forms a positive angle θ relative to a bottom side of a horizontal cross-sectional plane through the bottom component, which horizontal cross-sectional plane intersects the inner opening of the venting channel such that the angle θ ranges from greater than about 0° to less than about 90°, the angle θ being measured counter clockwise from the bottom side of the horizontal cross-sectional plane and having its vertex at the point of intersection of the inner opening and the horizontal cross-sectional plane; and iv. an opening at the top of the bottom component for accessing the bottom component;

b. a removable lid for covering the opening of the bottom component, the lid having a flow outlet channel positioned for receiving and permitting the outflow of fluid diffusing through the dentin sample from the flow inlet channel; and c. at least one washer adjacent to the lid and/or to the bottom component for securing the dentin sample within the flow cell.

B. a pumping mechanism for pumping a fluid into the flow cell through the flow inlet channel, through the dentin sample and out of the flow cell through the flow outlet channel; and C. at least one measuring device suitable for measuring and/or determining hydraulic conductance through a dentin sample.

Yet another embodiment of the present invention relates to a method for measuring the hydraulic conductance through a dentin sample, comprising the steps of:

A. providing a flow cell for measuring hydraulic conductance of dentin samples comprising:

a. a bottom component comprising:
i. an inner chamber;
ii. at least one flow inlet channel in flow communication with the inner chamber;
iii. at least one venting channel in flow communication with the inner chamber and having an inner opening where the venting channel joins with the inner chamber wherein the venting channel forms a positive angle θ relative to a bottom side of a horizontal cross-sectional plane through the bottom component, which horizontal cross-sectional plane intersects the inner opening of the venting channel such that the angle θ, ranges from greater than about 0° to less than about 90°, the angle θ being measured counter clockwise from the bottom side of the horizontal cross-sectional plane and having its vertex at the point of intersection of the inner opening and the horizontal cross-sectional plane; and
iv. an opening at the top of the bottom component for accessing the base portion, b. a removable lid for covering the opening of the bottom component, the lid having a flow outlet channel positioned for receiving and permitting the outflow of fluid diffusing through the dentin sample from the flow inlet channel; and c. at least one washer adjacent to the lid and/or to the bottom component for securing the dentin sample within the flow cell;

B. placing the dentin sample adjacent at least one washer;
C. sealing the flow cell with the removable lid;
D. providing a pumping mechanism for pumping a fluid into the flow cell through the flow inlet channel;

E. introducing a fluid into the flow cell such that the fluid fills the inner chamber and contacts the dentin sample;

F. tilting the flow cell such that a negative angle φ is formed relative to a top side of a horizontal cross-sectional plane through the bottom component to remove any accumulated air in the form of at least one air bubble generated after introduction of the fluid into the flow cell, which horizontal cross-sectional plane intersects the inner opening of the venting channel such that the angle φ ranges from greater than about 0°, the angle φ being measured clockwise from the top side of the horizontal cross-sectional plane and having its vertex at the point of intersection of the inner opening and the horizontal cross-sectional plane;

G. pumping the fluid into the flow cell through the flow inlet channel such that the fluid diffuses through the dentin sample and the flow outlet channel; and H. measuring the flow rate of the fluid pumped into the flow cell to determine the hydraulic conductance through dentin sample.

In another embodiment, the present invention relates to a flow cell, comprising:

i. a flow inlet channel having an inner opening, the flow inlet extending from the inner opening outwardly from the flow cell;

ii. a flow outlet channel in flow communication with the flow inlet channel; and iii. at least one reversible dentin sample securing mechanism positioned to secure a dentin sample between the flow inlet channel and the flow outlet channel, the dentin sample securing mechanism comprising a securing mechanism and at least one washer positioned adjacent the securing mechanism for receiving or contacting a dentin sample, the washer having at least one flat side for (optionally, leak free or substantially leak free) contact with a dentin sample.

In yet another embodiment, the present invention relates to a flow cell, comprising:

a. a bottom component comprising:
i. an inner chamber;
ii. at least one flow inlet channel in flow communication with the inner chamber;
iii. at least one flow outlet channel in flow communication with the flow inlet channel and the inner chamber; and
iv. an opening at the top of the bottom component for accessing the inner chamber, b. a removable lid for covering the opening of the bottom component, the lid having a flow outlet positioned for receiving and permitting the outflow of fluid diffusing through the dentin sample from the flow inlet channel; and c. at least one washer having at least one flat side for contacting a dentin sample or optionally at least one pair of flat sides, one flat side opposite (or substantially opposite) the other flat side, wherein one flat side of the washer contacts the lid and/or the bottom component and the other side of the pair of flat sides is positioned to contact the dentin sample for securing the dentin sample within the flow cell.

Another embodiment of the present invention relates to an apparatus for measuring hydraulic conductance of dentin samples, comprising;

a. a flow cell, comprising:
i. a flow inlet channel;
ii. a flow outlet channel in flow communication with the flow inlet channel; and iii. at least one reversible dentin sample securing mechanism positioned to secure a dentin sample between the flow inlet channel and the flow outlet channel, the dentin sample securing mechanism comprising a securing mechanism and at least one washer having at least one flat side for contacting a dentin sample or optionally at least one pair of flat sides, one flat side opposite (or substantially opposite) the other flat side, wherein one flat side of the pair of flat sides contacts the dentin sample and the other flat side of the pair of flat sides contacts the securing mechanism;

b. a pumping mechanism for pumping a fluid into the flow cell through the flow inlet channel, through the dentin sample and out of the flow cell through the flow outlet channel; and c. at least one flow meter for measuring the flow of fluid pumped into the flow cell and through the dentin sample.

In a further embodiment, the present invention relates to an apparatus for measuring hydraulic conductance of dentin samples, comprising;

a. a flow cell comprising;
   i. a flow inlet channel having an inner opening, the flow inlet extending from the inner opening outwardly from the flow cell:
   ii. a flow outlet channel in flow communication with the flow inlet channel; and
   iii. at least one dentin sample securing mechanism positioned to secure a dentin sample between the flow inlet channel and the flow outlet channel;

b. a pumping mechanism for exerting a pressure to pump a fluid into the flow cell through the flow inlet channel, through a dentin sample and out of the flow cell through the flow outlet channel;

c. a pressure regulator in flow communication with the pumping mechanism for regulating the pressure exerted by the pumping mechanism; and d. at least one flow meter in measuring contact with a fluid pumped by the pumping mechanism for directly measuring the flow rate of a fluid pumped into the flow cell and through the dentin sample.

A further embodiment of the present invention relates to an apparatus for measuring hydraulic conductance of dentin samples, comprising a fluid flow rate standardization mechanism, comprising:

i. a pumping mechanism for pumping a fluid through the apparatus;

ii. at least one adjustable high precision flow regulator for maintaining a pressure in the apparatus of less than or equal to 5 psi without fluctuations in the maintained pressure of greater than or equal to ±about 0.1 psi for a period of at least 10 minutes; and iii. at least one fluid flow meter for measuring the fluid flow rate across a dentin sample, wherein the fluid flow rate is standardized across different dentin samples for establishing a single fluid flow rate as the control against which the flow rate of the different dentin samples, after modification of the dentin samples, is compared.

Another embodiment of the present invention relates to a method for measuring the hydraulic conductance through a dentin sample, comprising the steps of:

a. providing a pumping mechanism for pumping a fluid through an apparatus;

b. pumping a fluid through the apparatus c. providing at least one adjustable high precision flow regulator for maintaining a pressure in the apparatus of less than or equal to 20 psi without fluctuations in the maintained pressure, for a period of at least 10 minutes, of greater than or equal to ±about 0.1 psi;

d. at least one fluid flow meter for measuring the fluid flow rate across a dentin sample;

e. directing the fluid flow through a dentin sample; and f. noting the fluid flow rate through the dentin sample indicated by the fluid flow meter wherein steps a. through f. are repeated for at least one other dentin sample and further wherein the flow regulator is adjusted such that the flow rate across the at least one other dentin sample(s) equals the flow rate of the first dentin sample.

Another embodiment of the present invention relates to an apparatus for measuring hydraulic conductance of dentin samples, comprising;

a. a flow cell comprising:
   i. a flow inlet channel;
   ii. a flow outlet channel in flow communication with the flow inlet channel; and
   iii. at least one dentin sample securing mechanism positioned between the flow inlet channel and the flow outlet channel;

b. a pumping mechanism for pumping a fluid into the flow cell through the flow inlet channel, through a dentin sample and out of the flow cell through the flow outlet channel;

c. a first flow rate meter in measuring contact with a fluid pumped by the pumping mechanism and calibrated to measure fluid flowing at a flow rate range of from about 0 microliters per minute to about 200 microliters per minute; and d. a second flow rate meter for measuring the flow rate of the fluid pumped by the pumping mechanism to confirm that a fluid pumped by the pumping mechanism is flowing at a rate within the flow rate calibration range of from about 0 microliters per minute to about 200 microliters per minute.

In a still further embodiment, the present invention relates to a method for measuring the hydraulic conductance through a dentin sample, comprising the steps of:

A. providing a flow cell for measuring hydraulic conductance of dentin samples comprising:
   a. a bottom component comprising:
      i. an inner chamber;
      ii. at least one flow inlet channel in flow communication with the inner chamber;
      iii. at least one venting channel in flow communication with the inner chamber;
      iv. an opening at the top of the bottom component for accessing the bottom component,
   b. a removable lid for covering the opening of the bottom component, the lid having a flow outlet channel positioned for receiving and permitting the outflow of fluid diffusing through the dentin sample from the flow inlet channel; and
   c. at least one washer adjacent to the lid and/or to the base for securing a dentin sample within the flow cell;

B. placing the dentin sample adjacent the washer of the flow cell;

C. providing a mechanism for pumping a fluid into the flow cell through the flow inlet channel;

D. pumping a fluid into the flow cell through the flow inlet such that the fluid diffuses through the dentin sample and the flow outlet channel;

E. providing a first flow rate meter in measuring contact with the fluid and calibrated to measure fluid flowing at a flow rate range of from about 0 microliters per minute to about 200 microliters per minute;

F. measuring the flow rate of the fluid pumped into the flow cell using the first flow rate meter to determine the hydraulic conductance through dentin sample;

G. providing a second flow rate meter;

H. measuring the flow rate of the fluid to confirm that the fluid is flowing at a rate within the flow rate calibration range; and I. determining the hydraulic conductance through the dentin sample.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which:

FIG. 1 is a vertical sectional view of the prior art flow cell for use in measuring the permeability of dentin with a dentin sample in place prior to the sealing of the cell;

FIG. 2 is a vertical sectional view of the flow cell of FIG. 1 with a dentin sample in place after the sealing of the flow cell;

DETAILED DESCRIPTION OF THE INVENTION

Figure 3:
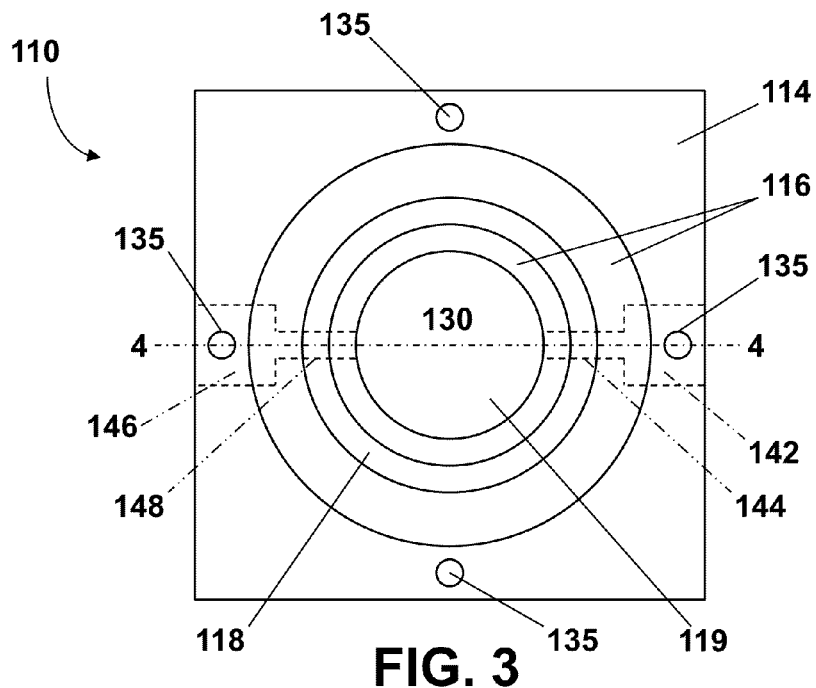
FIG. 3 is a top view of the bottom component of the flow cell for use in the present invention.

The devices, apparatus and methods of the present invention can comprise, consist of, or consist essentially of the essential elements and limitations of the invention described herein, as well any of the additional or optional components, or limitations described herein.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All patent documents incorporated herein by reference in their entirety are only incorporated herein to the extent that they are not inconsistent with this specification.

The term "flat" as used herein means having a horizontal surface without a slope, tilt, or curvature; or, having a smooth, even, level surface.

As used herein the phrase "reversible securing mechanism" means a securing mechanism which does not secure items (such as a dentin sample) permanently (i.e., as by gluing or cementing), but which after the item is secured, permits adjustment such that the item can be readily returned to its unsecured state. The present invention is a devices and methods for measuring the permeability of dentin.

FIG. 1 is a vertical sectional view of the prior art flow cell for use in measuring the permeability of dentin prior to sealing the flow cell. The prior art flow cell is generally cylindrical in shape. The figure shows the two-part cell with base component 10 and lid component 50. Lid component 50 includes inner surface 52, outer surface 54, screw threads 58 disposed on inner surface 52, and through-hole 56.

Base component 10 includes inner surface 12, outer surface 14, lip 16, screw threads 18 disposed on outer surface 14, and inlet 22 and outlet 24 channels. Inlet 22 and outlet 24 channels have "press-fit" connections to inlet and outlet tubes. As used herein, the term "press fit" (also referred to as "interference fit" or "friction fit") means the fastening of two parts achieved by friction between the parts after the parts are joined (e.g., as by pressing or pushing) together, instead of by any other type of fastening. The cylindrical shape of base component 10 defines inner chamber 20. The components which occupy inner chamber 20 of base component 10 for use in measuring the permeability of dentin sample 70 include top spacer 32 and bottom spacer 36, as well as "O"-rings 42 and 46 and larger sized "O"-rings 44, and 48. Top spacer 32 has through-hole 34, and bottom spacer 36 has through-hole 38.

The components which occupy inner chamber 20 of base component 10 of the prior art flow cell are assembled in the form of a stack as follows: bottom spacer 36 is placed on "O"-ring 48, which "O" ring 48 rests on the inner surface 12 of base component 10. "O"-rings 46 and 44 are placed on bottom spacer 36. Second side 74 of dentin sample 70 is placed on "O"-ring 46. "O"-ring 42 is placed on first side 72 of dentin sample 70. Top spacer 32 is placed on "O"-rings 42 and 44.

FIG. 2 shows the prior art flow cell after the sealing of the cell. To seal the cell, lid component 50 is screwed onto base component 10, with screw threads 58 disposed on inner surface 52 of lid component 50 matched with screw threads 18 disposed on outer surface 14, of base component 10.

The permeability of dentin sample 70 is measured using the prior art flow method and cell in the following manner. Once the two-part cell is assembled, outlet channel 24 is sealed. Pressure is used to induce fluid (e.g., distilled water) flow in inlet channel 22. Fluid flows into the portion of inner chamber 20 of base component 10 below dentin sample 70 from inlet channel 22. As the fluid pressure rises in the portion of inner chamber 20 below dentin sample 70, the fluid flows through through-hole 38 of bottom spacer 36. Increased fluid pressure then initiates fluid flow through (or across) the dentin sample 70 (i.e., through or across the dentin tubule or orifices in the dentin sample). Fluid flow continues through through-hole 34 of top spacer 32, and exits prior art flow cell through through-hole 56 of lid component 50.

The limitations of the Pashley method involve inherent inaccuracies in the Pashley flow cell. These inaccuracies include stacking error due to the number of flow cell components (i.e., the "O"-rings [four] and spacers [two]) as well as increased leaking potential. Leaks around the dentin sample are often caused by the user inaccurately placing the "O"-rings and spacers when assembling the cell. These leaks around the dentin sample result in an inaccurate measurement of permeability through the dentin.

Moreover, the "O"-rings used with the Pashley flow cell have round cross-sections. These "O"-rings have a single line of contact with the dentin sample once the components are arranged and the flow cell sealed as illustrated in FIG. 2. If the "O"-rings are formed of a "stiff" material, the risk of leakage in the system is increases. To alleviate this risk, the user typically adds extra vertical pressure to the "O"-rings when sealing the flow cell. Such additional vertical pressure, however, creates (or increases) the risk of damaging the dentin sample. On the other hand, if the "O"-rings are formed of a "soft" material, the "O"-rings will deform, and flatten against the dentin sample, changing the area of the dentin sample exposed to the fluid in the flow cell. Such inconsistency in the area of the dentin sample exposed to the fluid in the flow cell can result in inconsistent measurements of permeability through the dentin.

Another issue with the Pashley flow cell is that during the assembly of the cell, lid component 50 is screwed onto base component 10, with screw threads 58 disposed on inner surface 52 of lid component 50 matched with screw threads 18 disposed on outer surface 14, of base component 10, rotating lid component 50 relative to base component 10. The rotational movement of the lid component 50 with respect to the base component 10 often causes rotation of the dentin sample, the "O"-rings and/or the spacers, which can result in leaks (or increased leakage) around the dentin sample. These leaks around the dentin sample result in an inaccurate measurement of permeability through the dentin.

Yet another issue with the Pashley flow cell relates to the previously mentioned "press-fit" connections between inlet and outlet tubes and the inlet channel 22 and outlet 24 channel, respectively. Such "press-fit" connections often leak, especially under pressure, resulting in inaccuracies in flow rate measurements.

Furthermore, the Pashley method fails to provide for standardization of flow rates across a variety of different dentin samples when permeability data of more than one dentin sample is necessary or desired. Such standardizing of flow rates across different dentin samples would alleviate the need, in comparative analyses, to correct for such dentin sample variables as thickness and porosity. Typical dentin permeability flow rate methods measure the fluid flow rate across a particular dentin sample at a set generated (and maintained) pressure. For example, at a set pressure of, say, 0.75 psi, the fluid flow rate of one dentin sample might read 3 ul/min, but the fluid flow rate of a second dentin sample at the same (0.75 psi) pressure might read 10 ul/min, and the fluid flow rate of a third dentin sample at the same (0.75 psi) pressure might read 1 ul/min, etc. Differences in the mentioned dentin thickness and porosity variables primarily account for these fluid flow rate differences at a set (and maintained) pressure. To correct for these difference in fluid flow rates, the fluid flow rates of the different dentin samples are typically normalized. The term "normalized" as used herein means dividing every measurement for a given dentin sample by that sample's baseline (i.e., prior to treatment) flow rate measurement (see "Residual Permeability" formula at Example 1). By regulating the system pressures to less than or equal to 30 psi (or about 30 psi) and maintaining the system pressure with minimal fluctuation (i.e., less than or equal to ±0.1 psi) using a high precision pressure regulator, the present invention permits such standardization (i.e., establishing the same fluid flow rate for each dentin sample) across a variety of different dentin samples.

Figure 4:
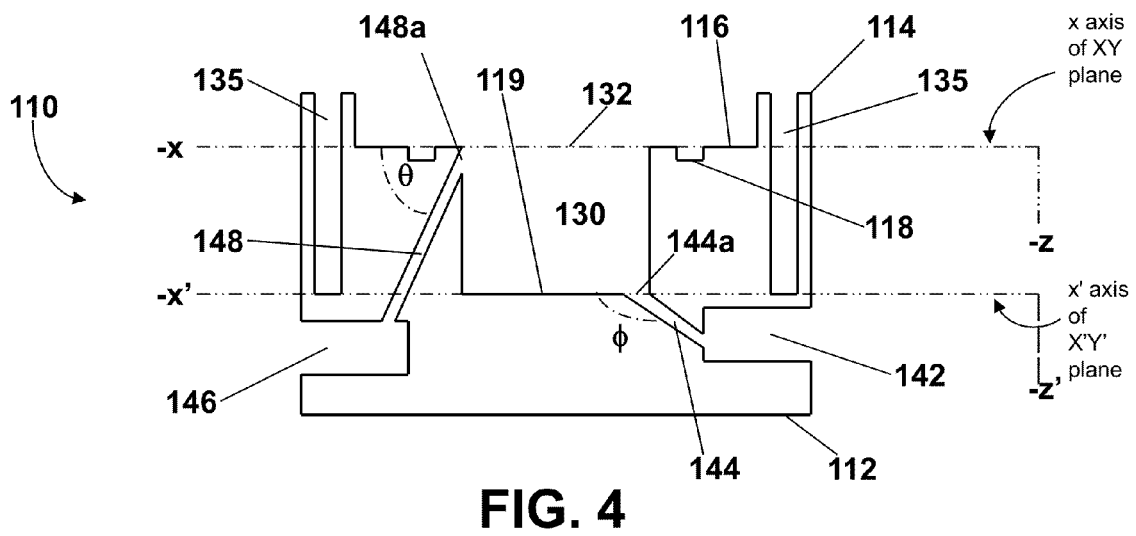
FIG. 4 is a vertical sectional view of FIG. 3 along the 4-4 plane.

FIGS. 3 through 8 are views of the two-part flow cell 100 for use in the present invention. FIG. 3 is a top view of the bottom component 110 of flow cell 100, while FIG. 4 is a vertical sectional view of FIG. 3 along the 4-4 plane. Bottom component 110 of the flow cell includes bottom surface 112, top surface 114, first indent 116, groove 118, second indent 119 which defines inner chamber 130, fastener blind holes 135 (or other suitable mechanism for engaging fasteners), inlet channel 144 in flow communication with optional secondary inlet channel 142, and venting channel 148 in flow communication with optional secondary venting channel 146. In certain embodiments, inlet channel 144 and venting channel 148 are positioned opposite or substantially opposite each other. Inlet channel 144 and venting channel 148 each have an inner end, 144a and 148a, respectively, the inner openings, 144a and 148a, joining inlet channel 144 and venting channel 148 to the inner chamber 130. The inner openings, 144a and 148a, further define the point from which inlet channel 144 and venting channel 148 extend outwardly from the flow cell 100. The bottom component 110 comprises an opening 132 at the top of the inner chamber 130 for accessing the inner chamber 130. Inlet channel 144 is positioned in flow communication with inner chamber 130. Venting channel 148 is also positioned in flow communication with inner chamber 130. Inlet channel 144 and venting channel 148 (or, if present, optional secondary inlet channel 142 and optional secondary venting channel 146) can be, optionally, threaded to receive the compatibly threaded ends of inlet and outlet tubes 238 and 254, respectively. Optionally, and as shown on the vertical cross-sectional view of the bottom compartment at FIG. 4, venting channel 148 forms a positive angle θ relative to a bottom side of a horizontal cross-sectional plane XY through the bottom component 110 and intersecting the inner end 148a of venting channel 148, angle θ having its vertex at the point of intersection of the inner end 148a and the horizontal cross-sectional plane XY. Angle θ, as measured from the bottom side of the horizontal cross-sectional plane XY counter clockwise (as illustrated at FIG. 4), ranges from greater than about 0° to less than about 90°, optionally from about 15 to about 75, optionally from about 35 to about 55, or, optionally about 60°. Optionally, and as shown on the vertical cross-sectional view of the bottom compartment at FIG. 4, inlet channel 144 forms a positive angle φ relative to a bottom side of a horizontal cross-sectional plane X'Y' through the bottom component 110 and intersecting the inner end 144a of inlet channel 144, angle φ having its vertex at the point of intersection of the inner end 144a and the horizontal cross-sectional plane X'Y'. Angle φ, as measured from bottom side of the horizontal cross-sectional plane X'Y' counter clockwise (as illustrated at FIG. 4), ranges from about 0° to less than or equal to about 270°, optionally from about 90° to about 180°, optionally from about 100° to about 130°, or, optionally about 116°. (For purposes of illustrating angles θ and φ, FIG. 4 shows the cross-sectional planes XY and X'Y' perpendicular to, and coming out of the paper along the x axis and the x' axis, respectively.)

Figure 5:
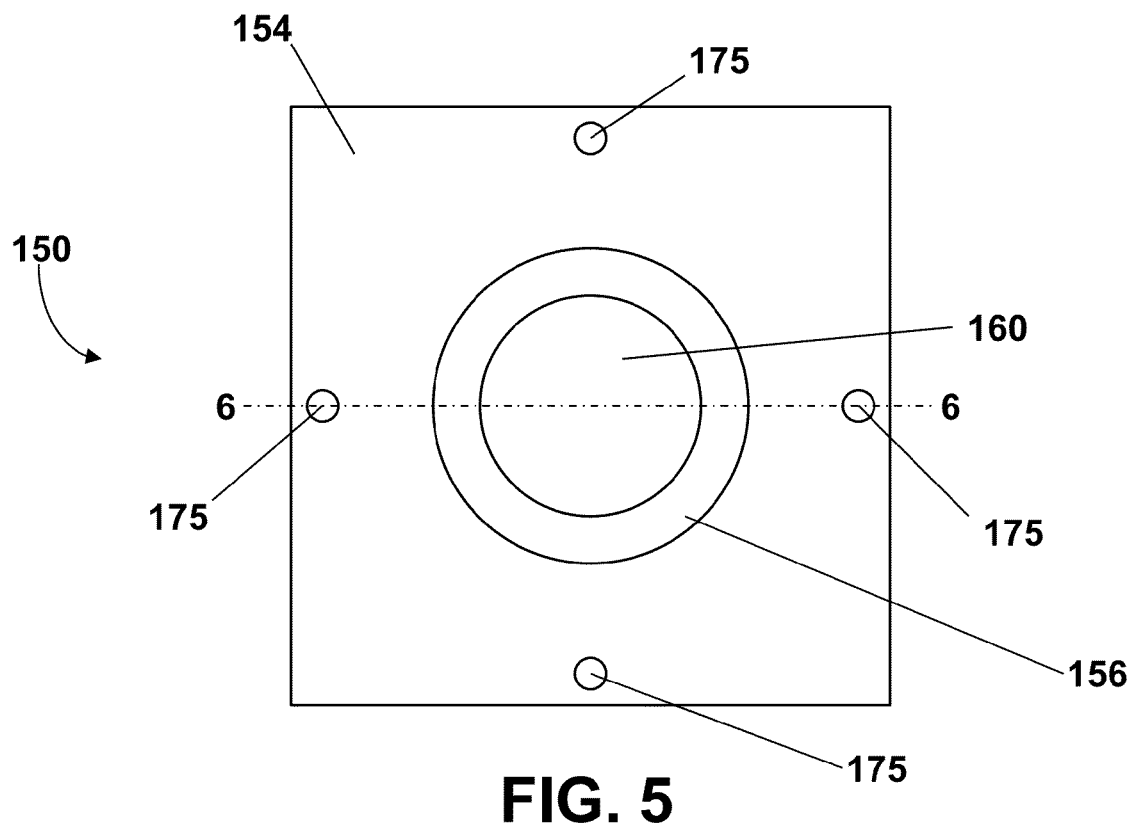
FIG. 5 is a top view of the top component of the flow cell for use in the present invention.
Figure 6:
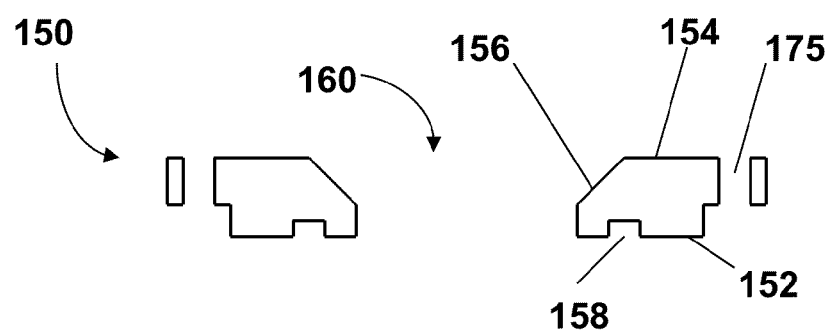
FIG. 6 is a vertical sectional view of FIG. 5 along the 6-6 plane.

FIG. 5 is a top view of the lid 150 for flow cell 100, while FIG. 6 is a vertical sectional view of FIG. 5 along the 6-6 plane. The lid 150 of the flow cell includes bottom surface 152, top surface 154, bottom groove 158, optional fastener through-holes 175 (or other suitable mechanism for engaging fasteners), and flow outlet channel 160. Flow outlet channel 160 is defined by walls 156 on lid 150 vertically, radially and conically skewed toward the center of the lid 150, increases the diameter of the out flow of fluid through flow outlet channel 160.

In certain embodiments, lid 150 and bottom component 110 are shaped to fit one in the other so as to permit a secure engagement between the two components. The lid 150 and bottom component 110 components may be formed from machined glasses; woods; metals, such as stainless steel; plastics, such as polymethyl methacrylate (PMMA) or polycarbonate (PC); or a combination of these materials. In one embodiment, lid 150 and bottom component 110 are formed from (e.g., by machining) optically clear or transparent PMMA, such as that available from MacMaster-Carr (Catalogue #8560K912 or #8560K265) of Robbinsville, N.J. The advantage of using a clear (e.g., optically clear or transparent) material in forming flow cell 100 is that clear materials allow "line of sight" into the cell or otherwise makes the contents of the cell visible to the unaided eye to, for example, help in visually determining whether all air in the form of air bubble(s) has been purged from the portion of inner chamber 130 below dentin sample 190 flows. An air bubble below dentin sample 190 decreases the area of dentin sample 190 through which fluid can flow through. As a reminder, the inability to consistently determine the area of the dentin sample exposed to the fluid flow cell 100 may result in an inconsistent measurement of permeability through the dentin.

Figure 7:
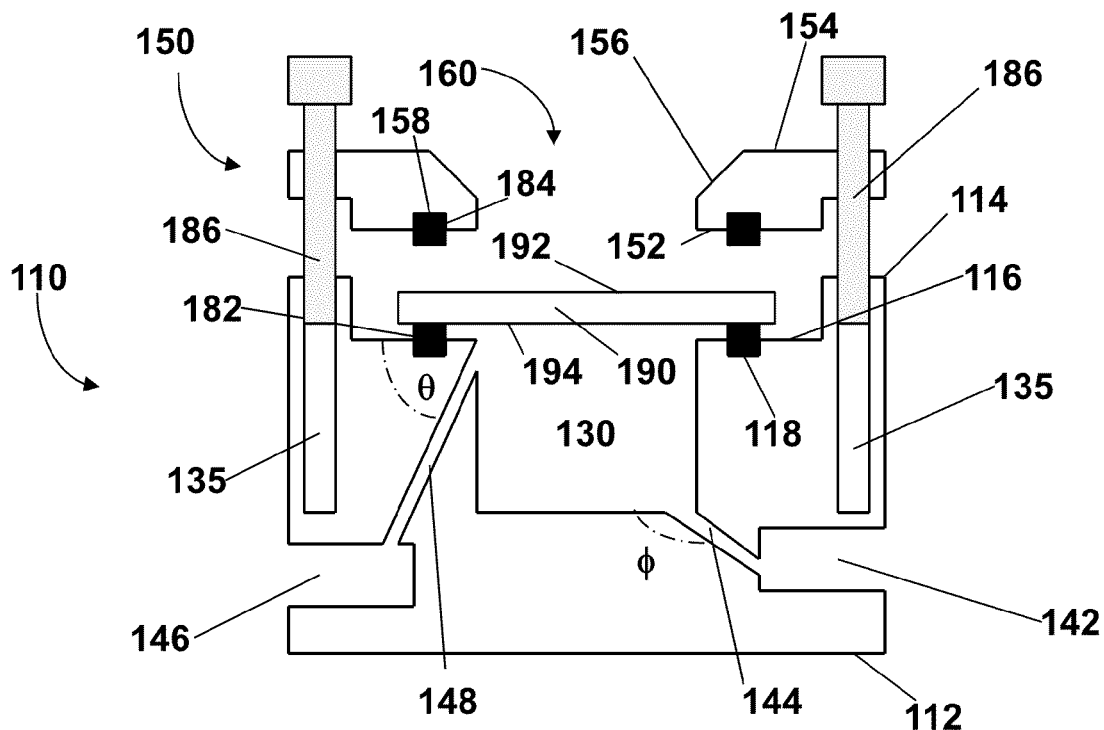
FIG. 7 is a vertical sectional view of the flow cell for use in the present invention with a dentin sample in place prior to the sealing of the cell.
Figure 8:
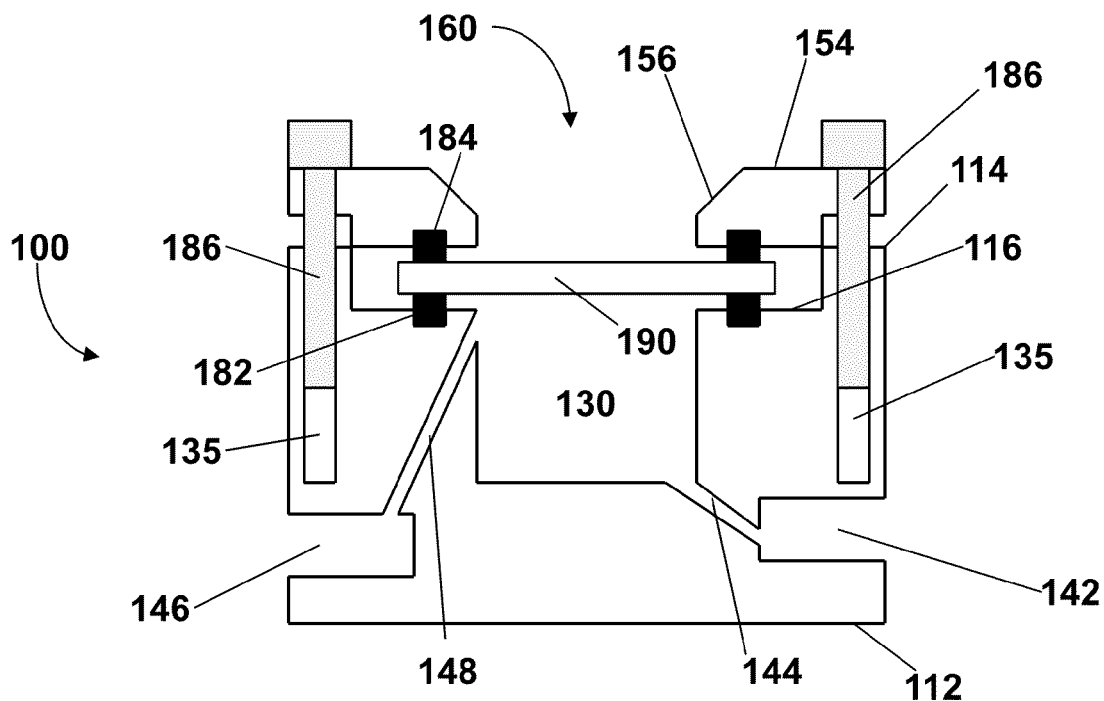
FIG. 8 is a vertical sectional view of the flow cell for use in the present invention with a dentin sample in place after the sealing of the cell.

FIG. 7 shows the flow cell for use in the present invention with dentin sample 190 in place prior to the sealing of the flow cell, while FIG. 8 shows the flow cell with a dentin sample in place after the sealing of the cell. The components which occupy the flow cell of the present invention include first and second washers 182 and 184, and dentin sample 190. Dentin sample 190 has first side 192 and second side 194.

The flow cell is assembled as follows. First washer 182 is placed in groove 118 of bottom component 110. Second washer 184 is placed in bottom groove 158 of lid 150. In certain embodiments, groove 118 of bottom component 110, and bottom groove 158 of lid 150 are machined to fit the width dimensions of any washer(s) used (such as washers 182 and 184) so as to reduce, minimize or prevent any displacement of the washer(s): i) as the components of the flow cell are being secured for use (e.g., testing and/or fluid flow measurement); and/or ii) during actual use (e.g., testing and/or fluid flow measurement). In other embodiments, groove 118 can be additionally machined so as to avoid obstructing or otherwise interfering with fluid and/or air bubble flow into and/or through venting channel 148. Second side 194 of dentin sample 190 is placed on first washer 182. Washer 184 is placed on first side 192 of dentin sample 190. To complete sealing of the cell, lid 150 is fastened onto bottom component 110, using fasteners 186. In the exemplified embodiment, the fasteners 186 are screws which pass through optional fastener through-holes 175 of lid 150 and are anchored in/by fastener blind holes 135 of bottom component 110 having screw holes suitable for engaging the screws so that the screws adjustably tighten and seal the lid 150 on to bottom component 110. The flow cell, including lid 150 and bottom component 110 is referred to as flow cell 100. Fasteners 186 may be formed of materials such as stainless steel. Fastener through-holes 175 and fastener blind holes 135 are machined to fit and engage fasteners 186.

Alternatively, the assembly of lid 150 on to bottom component 110 can be accomplished by the use of other adjustable fastening mechanisms, such as nails, dowels, clamps, straps, bolts (e.g., screw-type), or any other fastening mechanism suitable for providing a leak proof (or substantially leak proof) seal and allow for ready disassembly and assembly. Optionally, the fastening mechanism can operate by friction or interference fit so long as the friction or interference fit can withstand the fluid pressures necessary for practicing the present invention.

Figure 9:
FIG. 9 shows representative embodiments a to g of washers useful in the present invention.
Figure 9A:

The "washers" 182 and 184 of the present invention are have at least one flat side for contacting a dentin sample, optionally the washers are square washers or washers having at least one pair of flat sides, one flat side opposite (or substantially opposite) the other flat side of the pair, such that one flat side of the pair contacts the lid 150 and/or the base and the other flat side of the pair is positioned to contact a dentin sample for securing the dentin sample within the flow cell as illustrated in FIG. 8. In one embodiment, washers 182 and 184 of the present invention are "O" rings with square cross-sections as shown in FIG. 9a. First side (182' and 184') and second side (182" and 184") of washers 182 and 184 are flat.

Figure 9B:
Figure 9C:
Figure 9D:
Figure 9E:
Figure 9F:
Figure 9G:

Embodiments of washers useful in the present invention include, but are not limited to, such examples as shown in FIGS. 9a to 9g. FIG. 9a shows washer cross-sections 182a and 184a of a rectangular "O" ring. First side (182a' and 184a') and second side (182a" and 184a") of washer cross-sections 182a and 184a are flat. Washer cross-sections 182b and 184b of hexagonal "O" ring are shown in FIG. 9b. First side (182b' and 184b') and second side (182b" and 184b") of washer cross-sections 182b and 184b are flat. In FIG. 9c, washer cross-sections 182c and 184c of trapezoidal "O" ring. First side (182c' and 184c') and second side (182c" and 184c") of washer cross-sections 182c and 184c are flat. Washer cross-sections 182d and 184d of rounded rectangular "O" ring are shown in FIG. 9d. First side (182d' and 184d') and second side (182d" and 184d") of washer cross-sections 182d and 184d are flat. In FIG. 9e, washer cross-sections 182e and 184e of race-track shaped "O" ring. First side (182e' and 184e') and second side (182e" and 184e") of washer cross-sections 182e and 184e are flat. FIG. 9f shows washer cross-sections 182f and 184f of a single flat-sided "O" ring variant. Sides (182f" and 184f") of washer cross-sections 182f and 184f are flat. FIG. 9g shows washer cross-sections 182g and 184g of a single flat-sided "O" ring variant. Sides (182g" and 184g") of washer cross-sections 182g and 184g are flat. It should be understood that the shape of the cross-sections of washers 182 and 184 need not be the same, but may be independently different in shape such that washer 182 may have, for example, the cross-sectional shape illustrated at FIG. 9c and washer 184 may have the cross-sectional shape illustrated at FIG. 9g.

Washers 182 and 184 may be made of, silicon, rubber or soft plastic. Examples of such silicon, rubber or soft plastic materials, include, but are not limited to, butadiene rubber, butyl rubber, chlorosulfonated polyethylene, epichiorohydrin rubber, ethylene propylene diene monomer, ethylene propylene rubber, fluoroelastomer, nitrile rubber, perfluoroelastomer, polyacrylate rubber, polychloroprene, polyisoprene, polysulfide rubber, sanifluor, silicone rubber and styrene butadiene rubber) and thermoplastics (including, but not limited to, thermoplastic elastomer; thermoplastic polyolefin, thermoplastic polyurethane, thermoplastic etheresterelastomers, thermoplastic polyamide(s), melt processible rubber thermoplastic vulcanizate) and mixtures thereof. In one embodiment, the washers may be rubber "O"-rings supplied by McMaster-Carr (Catalogue #4061T114) of Robbinsville, N.J.

The permeability of dentin sample 190 is measured using flow cell 100 in the present invention in the following manner. Once the two-part flow cell 100 is assembled, pressure is used to initiate and maintain fluid (e.g., distilled water) flow in inlet channel 144, optionally via 1 secondary inlet channel 142. In the case FIG. 8, fluid flows from optional secondary inlet channel 142 into inlet channel 144, and into the portion of inner chamber 130 of bottom component 110 below dentin sample 190. Initially, venting channel 148 (and optional secondary venting channel 146), are kept open so that residual air in the form of air bubble(s) located in the portion of inner chamber 130 below dentin sample 190 flows into venting channel 148 and exits flow cell 100 (in some embodiments, through optional secondary channel 146). When the residual air has been removed, venting channel 148 (and/or optional secondary venting channel 146) is closed. When venting channel 148 (and/or optional secondary venting channel 146)

is closed, fluid pressure rises in the portion of inner chamber 130 below dentin sample 190. This increased fluid pressure initiates fluid flow in (across or through) the dentin tubule orifices in dentin sample 190. Fluid flow continues through flow outlet channel 160 of lid 150.

Without being limited by any of the enumerated theories, it is believed that the limitations of the Pashley cell are addressed by flow cell 100 of the present invention as follows. The stacking error found in the Pashley flow cell due to the excessive number of "O"-rings (four) and spacers (two) is eliminated by, in some embodiments, requiring no more than two washers in the flow cell 100. Also, by requiring grooves 118 and 158, flow cell 100 reduces, substantially eliminates or eliminates leaks around the dentin sample caused by sliding or inaccurate placement of the "O"-rings when assembling the Pashley cell.

Next, the washers used in flow cell 100 of the present invention have at least one flat side for contacting a dentin sample, optionally the washers have square cross-sections or at least one pair of flat sides, one flat side opposite (or substantially opposite) the other flat side of the pair, such that one flat side of the pair contacts the lid 150 and/or the base and the other flat side of the pair is positioned to contact a dentin sample for securing the dentin sample within the flow cell, whereas the "O"-rings used with the Pashley flow cell have round cross-sections. The oppositely situated flat side pairs of the washers of the present invention contact the dentin sample over a consistent area of the dentin sample, minimizing possible leaks in the system. Such washers also eliminate the inability to consistently determine the area of the dentin sample exposed to the fluid in the flow cell caused by varying width of the area of the sample/"O" ring contact line due to the flattening out of the round cross-section of the Pashley type "O"-rings when pressure is exerted during sealing of the Pashley cell. As a reminder, the inability to consistently determine the area of the dentin sample exposed to the fluid in the Pashley flow cell may result in an inconsistent measurement of permeability through the dentin when using the Pashley flow cell.

Another issue with the Pashley flow cell relates to the assembly of the Pashley flow cell, lid component 50 is screwed onto base component 10. The rotational movement of the lid component 50 with respect to the base component 10 often causes rotation of the dentin sample, the "O"-rings and the spacers, which can result in leaks around the dentin sample. In flow cell 100, leaks around dentin sample 190 are minimized by fastening lid 150 onto bottom component 110 using at least one press seal (i.e., a seal accomplished without rotational movement of the lid 150 relative to the bottom component 110) fastener 186.

Yet another issue with the Pashley flow cell relates to its "press-fit" connections from inlet and outlet tubes to the inlet 22 and outlet 24 channels. The "press-fit" connections often leak, resulting in inaccuracies in flow rate measurements. In certain embodiments, at least one of inlet channel 144; optional secondary flow inlet channel 142; venting channel 148 and optional secondary venting channel 146 used in flow cell 100 of the present invention have "threaded" connections to inlet and outlet tubes. Specifically, in some embodiments, at least one of inlet channel 144; optional secondary inlet channel 142; venting channel 148; and optional secondary venting channel 146 are machined so as to have "threaded" connections to inlet and outlet tubes via female or otherwise compatible treaded tube ends or adapters, such as those available from Upchurch—IDEX health and Science, Bristol, Conn. or Swagelok, Solon Ohio, and may be composed of metals such as stainless steel, polymers, or other non-reactive materials.

Figure 10:
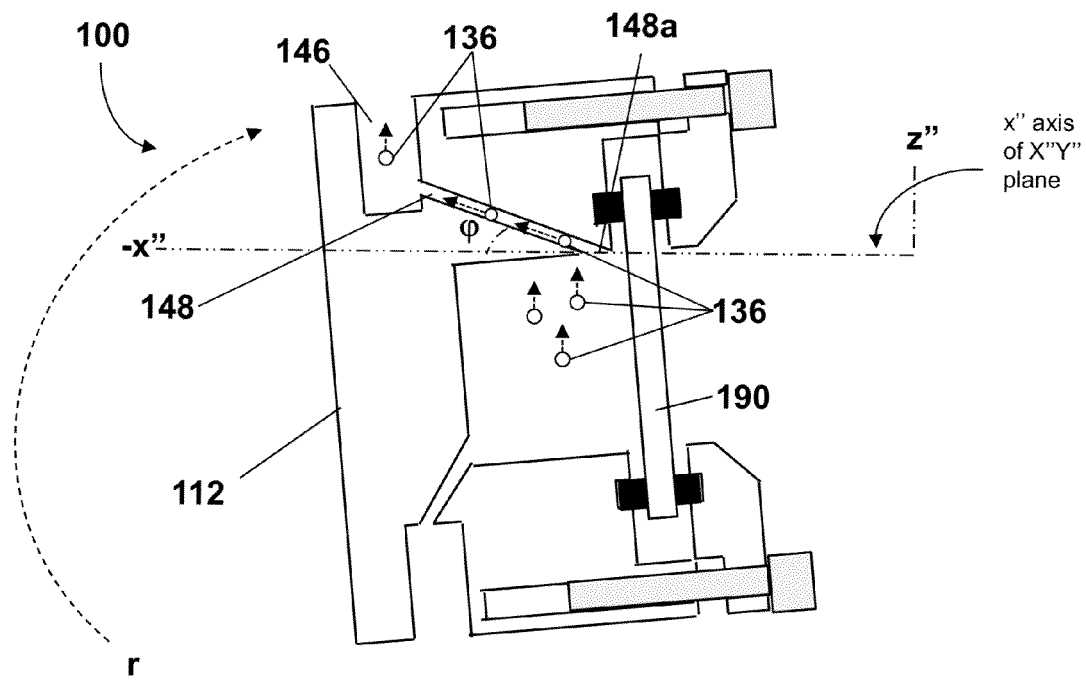
FIG. 10 is a flow cell positioned (e.g., as by rotation or tilting) to permit venting of air bubbles from the flow cell.

The Pashley method further fails to address the issue of air bubbles which tend to aggregate under the dentin samples in flow cells during dentin permeability measurements. Again, without being limited by theory in any of the following, it is believed that removal (or reduction) of air bubbles from below dentin sample 190 in inventive flow cell 100 is accomplished by positioning (e.g., by rotating or tilting) the cell such that the angled (by the angle θ) venting channel 148 forms a negative angle φ relative to a top side of a horizontal cross-sectional plane X"Y" through the flow cell 100 due to the positioning, the horizontal cross-sectional plane X"Y" intersecting the inner end 148a of venting channel 148 and angle φ having its vertex at the point of intersection of the inner end 148a and the horizontal cross-sectional plane X"Y". Angle φ, as measured from the top side of the horizontal cross-sectional plane X"Y" clockwise (as illustrated at FIG. 10), ranges from greater than about 0°, optionally from about 15° to about 85°, optionally from about 25° to about 55°, or optionally from about 30° to about 45°. As illustrated in FIG. 10, rotating or tilting the flow cell 100 clockwise (as illustrated by directional arrow "r") until venting channel 148 forms the described angle φ of greater than about 0° permits removal of air in the form of air bubble(s) 136. The lower density (relative to the fluid) air bubbles 136 (with directional arrows) flow in a vertical (or substantially vertical) direction (i.e., moving positively with respect to the illustrated z" axis) out from inner chamber 130, through venting channel 148 and optional secondary venting channel 146, and, then, out of the flow cell 100. (For purposes of illustrating angle φ, FIG. 10 shows the cross-sectional plane X"Y" perpendicular to, and coming out of the paper along the axis x".)

Figure 11:
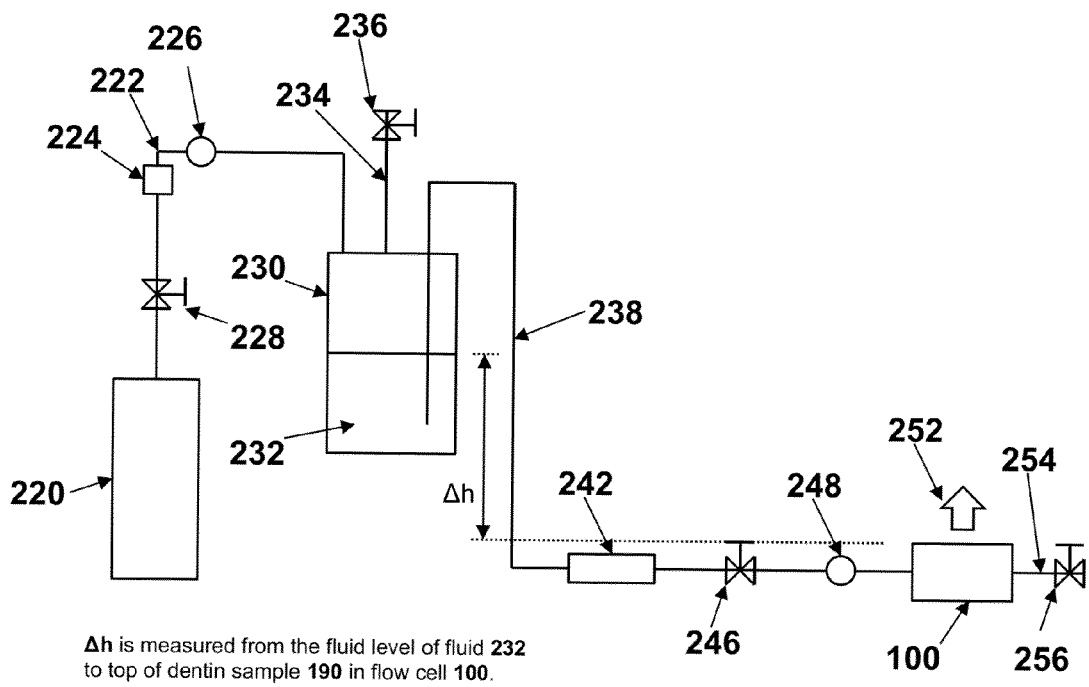
FIG. 11 is a schematic drawing of the equipment or system lay-out for the method of measuring the permeability of dentin according to the current invention.

FIG. 11 is a schematic flow chart drawing, explaining the equipment lay-out for use in the method of measuring the permeability of dentin according to the current invention. The figure shows flow cell 100, as a "black box" in the schematic drawing. Though this is one possible lay-out of for the equipment, it is to be understood that other possible lay-outs would also be useful in the method of measuring the permeability of dentin according to the current invention.

The schematic flow chart drawing includes, in flow communication: pressure generating tank 220; fluid source 230; flow meter 242; pressure regulator 224; pressure gauges 226 and 248; tubes 222, 234, 238, and 254; and valves 228, 236, 246, and 256. Tube 222 connects pressure generating tank 220 to fluid source 230. A fluid source 230 is provided having a vessel (or container) with a cross-sectional area large enough to prevent a detectable change in fluid level height from loss of fluid to the system apparatus. For example a liter vessel having a cross-sectional diameter of 10 cm could be used where the loss of fluid from the container during the measurement would about 0.5 ml, The vessel (or container) of fluid source 230 is filled with sufficient fluid 232 to define a fluid level plane perpendicular to the vessel (or container) wall. The fluid source 230 is positioned at a height Δh (i.e., the distance from the top of fluid level in the fluid source vessel to the top of the dentin sample in the flow cell 100). In certain embodiments, the Δh is chosen to provide a pressure (as determine by the static fluid pressure formula) comparable to pulpal pressure, namely from about 0.2 psi±0.05 psi. The static fluid pressure formula is ρgh, where ρ=m/V=fluid density, g=acceleration of gravity, and h (or, in the present case, Δh)=depth of fluid Fluid source 230 could be plastic, metal or glass. For example, fluid source 230 could be a one-liter media bottle supplied by Kimble Chase Life Science and Research Products LLC, Vineland, N.J., with a GL-45 Q-type Bottle cap 3way ¼-28 fitting ports (Fisher Scientific #00945Q-3). Fluid 232 may be water, distilled water, or de-ionized water (DI).

Pressurized inert gas flows from pressure generating tank 220 through valve 228, pressure regulator 224 and pressure gauge 226, and into the headspace above fluid 232 in fluid source 230. Tube 234 and valve 236 are located on and, as earlier noted, in flow communication with fluid source 230, and are used for venting fluid source 230, if necessary.

The pressurization of fluid source 230 by pressure generating tank 220 acting as a pumping mechanism (or source of pressure) for pumping fluid into flow cell 100. Other pumping mechanisms (or sources of pressure) include, but are not limited to, static fluid pressure, piston pumps, rotary piston pumps, diaphragm pumps, gear pumps, or double-action piston pumps.

The pressurization of fluid source 230 causes fluid 232 to exit fluid source 230 through tube 238. The fluid in tube 238 passes through flow meter 242, valve 246, and pressure gauge 248, and enters flow cell 100 through flow inlet channel 144 (or, optionally via secondary flow inlet channel 142) (see FIG. 8). Tube 254 is connected to and, as earlier noted, in flow communication with venting channel 148 (or, optionally via secondary vent channel 146 (see FIG. 8) of flow cell 100. Valve 256 is located on tube 254 to bleed residual air (or, air bubbles 136) located in the portion of inner chamber 130 below dentin sample 190 at the start of a dentin permeability measurement. Fluid exits flow cell 100 via through flow outlet channel 160 of lid 150 as shown by 252 in FIG. 11.

In one embodiment, the pressure generating tank 220 shown in the schematic drawing of FIG. 11 is a pressurized tank capable of providing a pressure in the apparatus, such as by stand alone laboratory tanks or air compressor. In certain embodiments, the pressure generating tank 220 provides pressure of up to 2000 psi. Such pressure generating tanks can be obtained from a number of known suppliers. Purified air could be used, as could be inert gases such as nitrogen or argon. In one embodiment, pressure generating tank 220 using nitrogen gas, either "high purity" or "ultra high purity" can be obtained from Air Gas, Radnor, Pa. An example of a pressure generating tank suitable for use in the present invention includes the N2 Cylinder HP300 supplied by Air Gas, Radnor, Pa. Optionally, the gas may be supplied from "house lines" external to the testing location, provided the pressure from the "house lines" is sufficient to perform the disclosed permeability test.

Pressure regulator 224 is an adjustable high precision regulator. As used herein, a "high precision regulator" means a regulator capable of maintaining a pressure of less than or equal to 30 psi (or about 30 psi), optionally less than or equal to 20 psi (or about 20 psi), optionally less than or equal to 15 psi (or about 15 psi), optionally less than or equal to 10 psi (or about 10 psi), optionally less than or equal to 5 psi (or about 5 psi), optionally less than or equal to 2.5 psi (or about 2.5 psi) and optionally from about 0.001 psi, optionally 0.01 psi (or about 0.01 psi), optionally 0.1 psi (or about 0.1 psi), optionally 0.25 psi (or about 0.25 psi), or optionally 0.5 psi (or about 0.5 psi), in all cases, without fluctuations, for a period of at least 10 minutes, optionally 15 minutes, optionally 30 minutes, or optionally 60 minutes. The term "fluctuation (s)" as used herein means measurement variation(s) of greater than or equal to ±0.1 psi (or about 0.1 psi), optionally greater than or equal to ±0.01 psi (or about ±0.01 psi), optionally greater than or equal to ±0.005 psi (or about 0.005 psi), or optionally greater than or equal to ±0.001 psi (or about 0.001 psi). In certain embodiments, the high precision regulator provides a pressure in the apparatus such that the fluid flow rate in the apparatus ranges from 0 (or about 0) to about 200, optionally from about 0 (or about 0) 0 (or about 0) to about 85, or optionally from about 0 (or about 0) to about 20 micro-liter/minute. An example of a high precision regulator suitable for use in the present invention is the Type-10LR pressure regulator supplied by Marsh Bellofram (Newell, W. Va.). Pressure gauges 226 and 248 may, in some embodiments, may be precision digital test gauges such as Types 2089, 2086, and 2084 supplied by Ashcroft (Huntington Beach, Calif.). Optionally, the apparatus of the present invention can employ at least two pressure regulators, a first gross pressure regulator capable of maintaining a pressure for a given or certain period of time and a second high precision pressure regulator capable of maintaining a pressure of less than or equal to 20 psi (or about 20 psi), optionally less than or equal to 15 psi (or about 15 psi), optionally less than or equal to 10 psi (or about 10 psi), optionally less than or equal to 5 psi (or about 5 psi), or optionally less than or equal to 2.5 psi (or about 2.5 psi), without fluctuations, for a period of at least 10 minutes, optionally 15 minutes, optionally 30 minutes, or optionally 60 minutes.

In one embodiment, the flow rate meter 242 is a high precision flow meter. When used to describe the flow rate meter, the phrase "high precision" means a flow meter having an instrument resolution of below about 0.5 microliter per minute, or optionally below about 0.5 nanoliters. The flow meter can be a manual or digital flow meter. Flow meter 242 acts as a measuring device suitable for measuring and/or determining hydraulic conductance through dentin sample 190. In certain embodiments, the flow rate meter is calibrated to measure fluid flow rates of from about 0 to about 200, optionally from about 0 to about 85, or optionally from about 0 to about 20 microliter/minute. Examples of manual flow rate meters that can be used include those supplied by Gilmont Instruments (Barrington, Ill.), including the direct reading flowmeter Gilmont Flowmeter GF2000 and the correlated flowmeter Gilmont Flowmeter GF3000. Examples of digital flow rate meters that can be used include the Sensirion SLG1430-025 flowmeter supplied by The Sensirion Co. (Westlake Village, Calif.) and such flow meters supplied by Bronkhorst High-Tech (Bethlehem, Pa.) as the thermal liquid mass flowmeter Micro-FLOW series L01 Digital Mass Flow Meter. In some embodiments, a second flow rate meter may be used with flow rate meter 242 to confirm that the fluid flow rate in the system of the present invention falls within the range that flow rate meter 242 is calibrated to measure (as described above). In other embodiments, one flow rate meter (manual) could be used to verify the more accurate reading of a second, digital flow rate meter.

Tubes 222, 234, 238, and 254, may be metal or plastic. In one embodiment, the tubes are Tube Tefzel (Natural 1/16× 0.040×50 ft), available from Upchurch—IDEX health and Science, Bristol, Conn. Valves 228, 236, 246, and 256 are used to control flow through the test apparatus, or to isolate sections of the test apparatus. The valves must be sized to fit with the rest of the test apparatus. In one embodiment, the valves are 2-Way Valve Bio with ⅛ in Fittings, available from Upchurch—IDEX health and Science, Bristol, Conn.

Because the permeability flow cell and hydraulic conductance system of the present invention addresses the inaccuracies and potential sources of leakage associated with the Pashley cell, it generally takes less than 5 (or about 5) minutes, optionally, less than 4 (or about 4) minutes, optionally, less than 3 (or about 3) minutes, or optionally less than 2 (or about 2) minutes for the apparatus' system to achieve stability of measurement. The phrase "stability of measurement", as used herein, means substantially no fluctuation in the fluid flow rate measurement readings, namely, no fluctuations in the fluid flow rate measurement readings of less than or equal to ±0.010 grams per hour, optionally less than or equal to ±0.005 grams per hour, or optionally less than or equal to ±0.001 grams per hour.

The present invention will be better understood from a consideration of the following illustrative examples.

EXAMPLES

The following examples are illustrative only and should not be construed as limiting the invention in any way. Those skilled in the art will appreciate that variations are possible which are within the spirit and scope of the appended claims.

Example 1

An in vitro study suing prepared dentin samples to evaluate treatment with formulations containing varying amounts of potassium oxalate (KO) as shown in Table 1.

Human dentin samples from molar teeth are used in the study. The samples are cut from the crown resulting in about one to three samples per tooth, each having a diameter of 10.7±0.5 mm and a thickness of 0.54+/−0.05 mm. The above cutting process leaves behind a smear layer on each surface of the dentin sample. The smear layer is removed by etching each dentin sample with 6% citric acid for 3 minutes in conjunction with sonication (sonications in this Example 1 and Example 2 were performed using a SharperTek CD-4800 ultrasonic cleaner supplied by Sharpertek USA [Pontiac, Mich.]). After etching, the dentin samples are again sonicated as described above in di-H$_2$O for 1.5 minutes to thoroughly clean the sample. The dentin samples, as described above, exhibit magnification properties when viewing through one side of the dentin sample and demagnification when viewing through the other side. The samples are stored in vials, magnification side facing upward, with a moistened towelette (i.e., Kimwipe with di-H$_2$O) within the capped vial to prevent the dehydration of the samples.

A. The system layout of FIG. 11 is prepared and primed for use in the permeation study as follows:
  A1. The following system units are turned on:
    pressure generating tank 220;
    flow meter (digital) 242; and
    pressure gauges 226 and 248;
  A2. Vent valve 236 is opened,
  A3. The dentin sample 190 is placed in flow cell 100, verifying that magnification side is facing upwards. The flow cell 100 is made of an optically clear material (i.e., clear acrylic),
  A4. A syringe is filled with di-H2O (DI) and connected to the flow cell inlet 144, the DI is present in the syringe at a volume equal to at least two times the volume of the fluid cell 100,
  A5. System valve 256 is opened to permit fluid introduced from the syringe to flow out,
  A6. Flow cell 100 is rotated about 45°, moving venting channel 148 upwards and inlet channel 144 downwards; The syringe is pressed in pulses to provide a fluid flow into the cell 100,
  A7. The syringe is pressed in pulses to provide a fluid flow into the cell 100,
  A8. Cell is rotated to view the bottom (i.e., demagnification side) of the dentin sample to verify the presence or absence of air bubbles;
  A9. Steps A7 and A8 are repeated until no air bubbles are present;
  A10. Once all air bubbles are removed, system valve 256 is closed and syringe is removed.
  A11. Cell 100 is connected via tubing 238 in flow communication with valve 246 and valve 246 is opened, (steps A3 to A11 take less than about 1 to 2 minutes). (When using the flow cell of the present invention, steps A3 to A11 should generally take no more than 5 minutes, optionally less than 3 minutes, optionally less than 2 minutes, optionally less than 1 minute.)
  A12. If the fluid flow (as measured by flow meter 242) is below about 15 microliter/min, under the head-pressure due to gravity (from Δh), valve 228 is opened providing pressure from pressure generating tank 220 for about 5-10 seconds and then valve 236 is closed,
  A13. Once valve 236 is closed, the pressure is adjusted via pressure regulator 224 to establish about 15 microliter/min fluid flow rate,
  A14. Once stable 15 microliter/min fluid flow rate is established, close valve 246,
  A15. The top surface of dentin sample 190 is dried with Kimwipe (or pipette) through flow outlet channel 160; preparing for commencement of Treatment Protocol
B. Treatment Protocol: A formulation of Table A is applied to the dentin sample of step A (above) as follows:
  B1. 200 microliters of the formulation is applied to dentin sample 190 using a pipette, and is left on the dentin sample for about 1 minute,
  B2. The formulation is, then, removed (or, taken up) from the dentin sample using a Kimwipe (or pipette), then 200 microliters of deionized (D.I.) water is applied onto dentin sample 190 using a pipette, and is left on the dentin sample for about 1 minute,
  B3. The DI water is, then, removed using a Kimwipe (or pipette),
  B4. Steps B1 through B3 are, then, repeated two additional times.
C. The permeation study with treated dentin sample 190 is performed using the pre-prepared/primed system of part A as follows (i.e.,):
  C1. Following steps of part A, system valve 246 is opened to start fluid flow;
  C2. The system is permitted to run for about 5 minutes to reach equilibrium for experimental fluid flow rate reading from fluid flow meter 242, and
  C3. System valve 246 is turned off.
D. Treatment Protocol (Steps B1 to B4) and Permeation Study (Steps C1 to C3) are repeated for each formulation in Table 1 until the earliest of: i) the flow rates of all 15 treatments are measured (i.e., mimicking about 1 week of use); or ii) no flow rate is observed through the dentin sample.

The data is normalized by calculating the residual permeability (RP). The RP of dentin sample after a treatment is calculated as follows:

$$RP_x = \frac{\text{Flow Rate}_x}{\text{Flow Rate}_0}$$

where: Flow Rate$_x$ is the measured flow rate after each of x treatments (0 to n), where n is the total number of treatments, and Flow Rate$_0$ is the measured flow rate prior to any treatment.

Though typically presented in terms of RP, this step may be omitted when using the apparatus (including flow cell) and methods of the present invention in view of present invention's ability to standardize flow rates (e.g, at 15 microliters/min) across each dentin sample.

The formulations of Table 1 were prepared using conventional mixing technology.

TABLE 1

Dentin Sample Treatment Formulations

Formulations based on Potassium Oxalate (KO) Content

| Ingredient | 0.5% KO Concentration (%) | 1.0% KO Concentration (%) | 1.5% KO Concentration (%) | 2.0% KO Concentration (%) | 0.0a% KO Concentration (%) | 0.0b% KO Concentration (%) |
|---|---|---|---|---|---|---|
| 190 proof ethyl alcohol | 22.6530 | 22.6530 | 22.6530 | 22.6530 | 22.6530 | 22.6530 |
| Menthol | 0.0323 | 0.0323 | 0.0323 | 0.0323 | 0.0323 | 0.0323 |
| Thymol | 0.0639 | 0.0639 | 0.0639 | 0.0639 | 0.0639 | 0.0639 |
| Methyl Salicylate | 0.0660 | 0.0660 | 0.0660 | 0.0660 | 0.0660 | 0.0660 |
| Eucalyptol | 0.0922 | 0.0922 | 0.0922 | 0.0922 | 0.0922 | 0.0922 |
| Flavor | 0.0850 | 0.0850 | 0.0850 | 0.0850 | 0.0850 | 0.0850 |
| Poloxamer 407 | 0.2500 | 0.2500 | 0.2500 | 0.2500 | 0.2500 | 0.2500 |
| Sorbitol Solution, 70% | 20.0000 | 20.0000 | 20.0000 | 20.0000 | 20.0000 | 20.0000 |
| Sucralose NF | 0.0300 | 0.0500 | 0.0300 | 0.0300 | 0.0300 | 0.0300 |
| Potassium Oxalate | 0.5000 | 1.0000 | 1.5000 | 2.0000 | — | — |
| Sodium Fluoride | 0.0221 | 0.0221 | 0.0221 | 0.0221 | 0.0221 | — |
| Dye | 0.0005 | 0.0005 | 0.0005 | 0.0005 | 0.0005 | 0.0005 |
| Deionized Water | QS to 100 | QS to 100 | QS to 100 | QS to 100 | QS to 100 | QS to 100 |
| pH | 3.5 | 3.5 | 3.5 | 3.5 | 3.5 | 3.5 |

Table 2 shows the formulations used in the study, as well as the residual permeability after every three treatments (with Standard Deviation [SD] of measurement). Formulations labeled "0.0a" and "0.0b" were controls.

TABLE 2

Residual Permeability of Potassium Oxalate treated dentin samples.

Number of Treatments (Residual Permeability ± SD)

| % KO | 0 | 3 | 6 | 9 | 12 | 15 |
|---|---|---|---|---|---|---|
| 0.5 | 1.000 ± 0.000 | 0.872 ± 0.127 | 0.832 ± 0.142 | 0.723 ± 0.194 | 0.603 ± 0.241 | 0.467 ± 0.255 |
| 1.0 | 1.000 ± 0.000 | 0.814 ± 0.106 | 0.542 ± 0.223 | 0.304 ± 0.198 | 0.152 ± 0.123 | 0.073 ± 0.055 |
| 1.5 | 1.000 ± 0.000 | 0.506 ± 0.075 | 0.113 ± 0.022 | 0.025 ± 0.004 | 0.018 ± 0.002 | 0.017 ± 0.004 |
| 2.0 | 1.000 ± 0.000 | 0.336 ± 0.044 | 0.050 ± 0.007 | 0.022 ± 0.005 | 0.019 ± 0.002 | 0.019 ± 0.002 |
| 0.0a | 1.000 ± 0.000 | 0.997 ± 0.003 | 0.990 ± 0.007 | 0.973 ± 0.021 | 0.966 ± 0.029 | 0.955 ± 0.045 |
| 0.0b | 1.000 ± 0.000 | 1.032 ± 0.006 | 1.041 ± 0.017 | 1.054 ± 0.016 | 1.056 ± 0.015 | 1.060 ± 0.017 |

SD = Standard Deviation

The table shows that as the number of treatments increases, the residual permeability (or, permeability of the dentin samples) decreases for all KO containing formulations. In addition, as the KO percent in the treatment formulation increases, the rate of decrease of the residual permeability increases. The reduction of residual permeability of dentin after treatments corresponds to occlusion efficacy of treatment technology. The residual permeability may be plotted as a function of treatments and compared against control/other formulations. The results further indicate that the high throughput apparatus and methods of the present invention do not compromise integrity of the generated data.

Example 2

The versatility of the high throughput apparatus (including the flow cell) and methods of the present invention is further illustrated by its use in the treatment "challenge" procedure described below. The time period from the removal of the dentin sample from the inventive flow cell to obtaining reliable flow rate data (after reincorporation of the dentin sample into the inventive flow cell and apparatus according to the procedure outlined below) can be less than 5 minutes, optionally 3 minutes, optionally 2 minutes, or optionally 1 minute.

The reliability of the flow rate data results from the dependability, reliability and predictability of the setup and the performance of the apparatus (including the flow cell) of the present invention, coupled with the recognition that data integrity is not compromised.

Treatment Challenge Procedure

The treatment technologies applied to dentin samples (e.g., the formulations of Table 1) can be challenged (i.e., brushing, acid, sonication etc., alone or in combination) and, then, evaluated using the flow cell, apparatus and methods of the present invention using the following procedure:

E. Performing step A1 through D of Example 1, followed by:

E1. The top of flow cell 100 is removed from the bottom component of flow cell, E2. The washer location on the dentin sample is marked, (this step can also be performed after step A3 in Example 1).

E3. The dentin sample is removed from the flow cell 100,

E4. The dentin sample is challenged by placing dentin sample into a vial of hydrodroxylapatite saturated lactic acid (~pH=5.0) and sonicated for about 90 seconds, E5. The dentin sample is rinsed in a pool of DI, E6. Steps A3 through A11 of Example 1 are performed to prime (i.e., remove air bubbles) the flow cell 100 and reestablish conductivity of apparatus system, E7. The fluid flow rate is then obtained from flow rate meter 242.

The time period from the removal of the dentin sample from the flow cell to obtaining flow rate measurement data takes less than 2 minutes and, in some cases, less than 1 minute.

What is claimed is:

1. A flow cell for measuring hydraulic conductance of dentin samples, comprising:
   a. a flow inlet channel;
   b. a flow outlet channel in flow communication with the flow inlet channel;
   c. at least one dentin sample securing mechanism positioned between the flow inlet channel and the flow outlet channel for securing a dentin sample; and
   d. at least one venting channel having an inner opening from which the venting channel extends outwardly from the flow cell, the venting channel positioned for receiving any air in the form of at least one air bubble that might accumulate under a dentin sample secured by the securing mechanism, after introduction of a fluid into the flow cell through the flow inlet channel, wherein the venting channel forms a positive angle $\theta$ relative to a bottom component of a horizontal cross-sectional plane through the bottom component, which horizontal cross-sectional plane intersects the inner opening of the venting channel such that the angle $\theta$ ranges from greater than 0° to less than 90°, the angle $\theta$ being measured counter clockwise from the bottom side of the horizontal cross-sectional plane and having its vertex at the point of intersection of the inner opening and the horizontal cross-sectional plane.

2. The flow cell according to claim 1 wherein the angle $\theta$ ranges from about 15° to about 75°.

3. The flow cell according to claim 2 wherein the angle $\theta$ ranges from about 35° to about 55°.

4. The flow cell according to claim 1 further comprising a secondary venting channel positioned opposite the inner opening of the venting channel in flow communication with the venting channel.

5. The flow cell according to claim 1 further comprising a secondary inlet channel positioned opposite the inner opening of the inlet channel in flow communication with the inlet channel.

6. The flow cell according to claim 1 wherein the dentin sample securing mechanism is reversible.

7. The flow cell according to claim 6 wherein the dentin sample securing mechanism comprises at least one washer.

8. The flow cell according to claim 6 wherein the dentin sample securing mechanism comprises at least two washers.

9. A flow cell for measuring hydraulic conductance of a dentin sample, comprising:

A. a bottom component comprising:
   i. an inner chamber;
   ii. at least one flow inlet channel in flow communication with the inner chamber;
   iii. at least one flow outlet channel in flow communication with the flow inlet channel and the inner chamber;
   iv. at least one venting channel in flow communication with the inner chamber and having an inner opening where the venting channel joins with the inner chamber; and
   v. an opening at the top of the bottom component for accessing the inner chamber, B. a removable lid for covering the opening of the bottom component, the lid having a flow outlet channel positioned for receiving and permitting the outflow of fluid diffusing through (or across) the dentin sample from the flow inlet channel; and C. at least one washer adjacent to the lid and/or to the bottom component for securing the dentin sample within the flow cell, wherein the venting channel forms a positive angle $\theta$ relative to a bottom side of a horizontal cross-sectional plane through the bottom component, which horizontal cross-sectional plane intersects the inner opening of the venting channel such that the angle $\theta$ ranges from greater than 0° to less than 90°, the angle $\theta$ being measured counter clockwise from the bottom side of the horizontal cross-sectional plane and having its vertex at the point of intersection of the inner opening and the horizontal cross-sectional plane.

10. An apparatus for measuring hydraulic conductance of dentin samples, comprising;

A. a flow cell comprising:
   a. a bottom component comprising:
   i. an inner chamber;
   ii. at least one flow inlet channel in flow communication with the inner chamber;
   iii. at least one venting channel in flow communication with the inner chamber and having an inner opening where the venting channel joins with the inner chamber wherein the venting channel forms a positive angle $\theta$ relative to a bottom side of a horizontal cross-sectional plane through the bottom component, which horizontal cross-sectional plane intersects the inner opening of the venting channel such that the angle $\theta$ ranges from greater than 0° to less than 90°, the angle $\theta$ being measured counter clockwise from the bottom side of the horizontal cross-sectional plane and having its vertex at the point of intersection of the inner opening and the horizontal cross-sectional plane; and
   iv. an opening at the top of the bottom component for accessing the bottom component;
   b. a removable lid for covering the opening of the bottom component, the lid having a flow outlet channel positioned for receiving and permitting the outflow of fluid diffusing through the dentin sample from the flow inlet channel; and
   c. at least one washer adjacent to the lid and/or to the bottom component for securing the dentin sample within the flow cell.

B. a pumping mechanism for pumping a fluid into the flow cell through the flow inlet channel, through the dentin sample and out of the flow cell through the flow outlet channel; and C. at least one measuring device suitable for measuring and/or determining hydraulic conductance through a dentin sample.

11. A method for measuring the hydraulic conductance through a dentin sample, comprising the steps of:

A. providing a flow cell for measuring hydraulic conductance of dentin samples comprising:
a. a bottom component comprising:
i. an inner chamber;
ii. at least one flow inlet channel in flow communication with the inner chamber;
iii. at least one venting channel in flow communication with the inner chamber and having an inner opening where the venting channel joins with the inner chamber wherein the venting channel forms a positive angle $\theta$ relative to a bottom side of a horizontal cross-sectional plane through the bottom component, which horizontal cross-sectional plane intersects the inner opening of the venting channel such that the angle $\theta$, ranges from greater than 0° to less than 90°, the angle $\theta$ being measured counter clockwise from the bottom side of the horizontal cross-sectional plane and having its vertex at the point of intersection of the inner opening and the horizontal cross-sectional plane; and
iv. an opening at the top of the bottom component for accessing the base portion,
b. a removable lid for covering the opening of the bottom component, the lid having a flow outlet channel positioned for receiving and permitting the outflow of fluid diffusing through the dentin sample from the flow inlet channel; and
c. at least one washer adjacent to the lid and/or to the bottom component for securing the dentin sample within the flow cell;
B. placing the dentin sample adjacent at least one washer;
C. sealing the flow cell with the removable lid;
D. providing a pumping mechanism for pumping a fluid into the flow cell through the flow inlet channel;
E. introducing a fluid into the flow cell such that the fluid fills the inner chamber and contacts the dentin sample;
F. tilting the flow cell such that a negative angle $\phi$ is formed relative to a top side of a horizontal cross-sectional plane through the bottom component to remove any accumulated air in the form of air bubbles generated after introduction of the fluid into the flow cell, which horizontal cross-sectional plane intersects the inner opening of the venting channel such that the angle $\phi$ ranges from greater than 0°, the angle $\phi$ being measured clockwise from the top side of the horizontal cross-sectional plane and having its vertex at the point of intersection of the inner opening and the horizontal cross-sectional plane;
G. pumping the fluid into the flow cell through the flow inlet channel such that the fluid diffuses through the dentin sample and the flow outlet channel; and
H. measuring the flow rate of the fluid pumped into the flow cell to determine the hydraulic conductance through dentin sample.

* * * * *